United States Patent [19]
Bissinger et al.

[11] Patent Number: 5,674,721
[45] Date of Patent: Oct. 7, 1997

[54] PROCESS FOR MAKING YEAST CELLS RESISTANT TO EXTREME HIGH PRESSURE

[76] Inventors: Peter H. Bissinger, 2-58 Darlington Drive, Sherrybrook, New South Wales 2113, Australia; Robert H. Schiestl, 6 Furnival Rd., Boston, Mass. 02130; John F. Davidson, 11 Adelaide St. No. 2, Jamaica Plain, Mass. 02130

[21] Appl. No.: 235,569

[22] Filed: Apr. 29, 1994

Related U.S. Application Data

[63] Continuation-in-part of Ser. No. 926,949, Aug. 10, 1992, abandoned.
[51] Int. Cl.$^6$ .............. C12N 15/52; C12N 1/18; C12N 1/19; C12N 15/09
[52] U.S. Cl. ................. 435/172.3; 435/254.11; 435/254.21
[58] Field of Search .......... 435/254.11, 254.21, 435/172.3

[56] References Cited

U.S. PATENT DOCUMENTS

| | | | |
|---|---|---|---|
| 4,439,523 | 3/1984 | Malick et al. | 435/243 |
| 4,742,004 | 5/1988 | Hartman et al. | 435/189 |

OTHER PUBLICATIONS

Stringer (1993) "Identity of Pneumocystis carinii not a single protozoan, but a diverse group of exotic fringe" Infectious Agents and Disease —Reviews 2:109–117 (Abstract only).
Romanos et al. (1992) "Foreign gene expression in yeast: A review" Yeast 8: 423–488.
Lepock et al. (1985) "Structural analyses of varions Cu, Zn–Superoxide dismetric by differential scanning calorimetry and Roman spectroscopy", Arch. Biochem Biophys. 241:243–251.
Bermingham McDonogh et al (1988) "The copper, zinc superoxide dismitase gene of saccharomyces derivisea: Cloning, sequencing and biological activity": Proc. Natl. Acad. Sci 85:4789–4793.
Farr et al. (1991) "Oxidative stress responses in Escherichia coli and Selmonella typhinuriun", Microbiol. Rev. 55:561–585.
Kono et al. (1982) "Superoxide radical inhibits catalase". J. Biol. Chem. 257:5751–5754.
Lin et al (1992) "Increase in superoxide production by heat-shocked cells of Neurospora cressa demonstrated by the fluorometric assay" Int. J. Biochem. 24:1081–1086.
Wieser, R. (1991) "Heat shock Factor–independent heat control of transcription of the CTTI gene encoding the cytosolic catalase T of S.cerevisiae", J. Biol. Chem. 266: 12406–12411.

*Primary Examiner*—Jasemine C. Chambers
*Assistant Examiner*—Scott D. Priebe
*Attorney, Agent, or Firm*—Howard J. Greenwald

[57] ABSTRACT

Novel dividing cells of the yeast Saccharomyces. A first portion of dividing yeast cells is transformed with DNA encoding superoxide dismutase protein and DNA encoding catalase protein, and a second portion of yeast cells is not transformed with DNA grown at the same cell density as the first portion. When both portions of cells are heated in the presence of oxygen containing gas to a temperature of 50 degrees Celsius and are maintained at such temperature for 20 minutes, at least twice as many cells of the first portion of cells survive.

7 Claims, 4 Drawing Sheets

PROCESS FOR MAKING YEAST CELLS RESISTANT TO EXTREME HIGH PRESSURE

CROSS REFERENCE TO RELATED APPLICATIONS

This is a continuation-in-part of patent application Ser. No. 07/926,949, filed Aug. 10, 1992, now abandoned.

FIELD OF THE INVENTION

A process for protecting living fungal cells against the adverse effects of extreme temperatures in which the fungal cells are grown under anaerobic conditions and/or genes coding for the expression of catalase enzyme and superoxide dismutase enzyme are incorporated into the fungal cells.

BACKGROUND OF THE INVENTION

Many fungal cells which are used in commercial processes (such as yeast cells) are sensitive to extremes of temperature. Thus, by way of illustration, when yeast cells are exposed to a temperature in excess of 50 degrees Celsius for at least 5 minutes, more than 99 percent of the yeast cells will die. See, e.g., an article by Yolanda Sanchez et al. appearing in The EMBO Journal, volume 11, number 66, pages 2357–2364 (1992).

It is known that Saccharomyces cerevisiae yeast contain a "CTT1" gene which codes for the an enzyme known as "Catalase T." This enzyme appears to afford some protection to the yeast against "lethal heat shock," i.e., exposure to a temperature of 50 degrees centigrade for 20 minutes. A standard laboratory strain of such yeast, when exposed to such conditions, will have a mortality frequency of 99.978 percent. By comparison, an isogenic strain of such yeast which lacks the CTT1 gene will have a mortality frequency under the same conditions of 99.993 percent. See, e.g., an article by Rotraud Wieser et al. entitled "Heat Shock Factor-independent Heat Control of Transcription of the CTT1 gene Encoding the Cytosolic Catalase T of Saccharomyces cerevisiae" appearing at pages 12406–12411 of The Journal of Biological Chemistry, Volume 266, No. 19 (1991).

It is an object of this invention to provide a process for increasing the protection of living fungal cells against extremes of temperature.

It is yet another object of this invention to provide a novel intermediate for the production of living fungal cells with increased resistance to extremes of temperature.

It is yet another object of this invention to provide a second process for increasing the protection of living fungal cells against extremes of temperature.

SUMMARY OF THE INVENTION

In accordance with this invention, there is provided a process in which genes coding for superoxide dismutase and catalase are both incorporated into living fungal cells.

In the first step of this process, two genes, coding for superoxide dismutase and catalase, are introduced into the fungal organism, or the selection of mutants that increase the activity of one or both enzymes.

In further accordance with this invention, there is also provided a second process for producing temperature resistant fungal cells by growing fungal cells anaerobically.

BRIEF DESCRIPTION OF THE DRAWINGS

The present invention will be more fully understood by reference to the following detailed description thereof, when read in conjunction with the attached drawings, wherein like reference numerals refer to like elements, and wherein.

DESCRIPTION OF THE PREFERRED EMBODIMENTS

Figure 1:
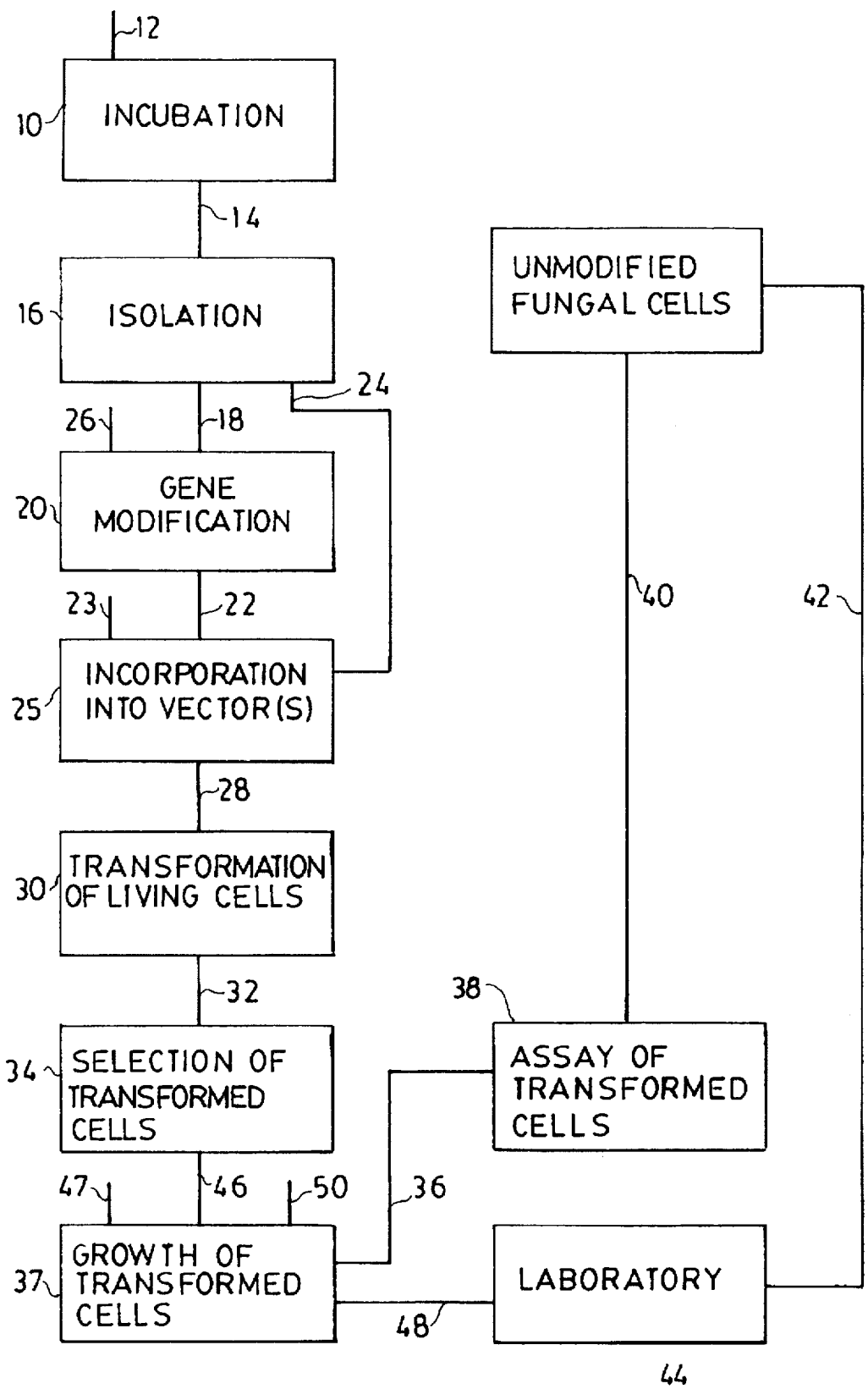
FIG. 1 is a flow chart illustrating one preferred embodiment of applicants' process.

FIG. 1 is a flow diagram illustrating one preferred embodiment of applicants' invention. In the first step of the process, cells which contain the superoxide dismutase gene and/or the catalase gene are grown in incubator 10.

As is known to those skilled in the art, superoxide dismutase is that enzyme which catalyzes the reaction $2O_2^- + 2H^+ = H_2O_2 + O_2$. The enzyme appears to be ubiquitous among aerobic organisms and protects the organism against action by the superoxide radical ($O_2^-$), which is believed to be a mutagenic substance.

The superoxide dismutase enzyme is classified in International Enzyme nomenclature as CE 1.15.1.1.

There are three known forms of superoxide dismutase (SOD) containing different metals in the protein molecules, iron, manganese, or both copper and zinc. All of them catalyze the same reaction with ultimate efficiency, and all operate with a mechanism in which the metal is the catalytic factor in the active site. The enzymes fall into several evolutionary groups. The manganese and iron SOD's are found primarily in prokaryotic cells and mitochondria, while copper zinc SOD has been demonstrated in virtually all eukaryotic organisms. Reference may be had to U.S. Pat. No. 4,742,004, the entire disclosure of which is hereby incorporated by reference into this specification.

Referring again to FIG. 1, cells containing a gene coding for SOD may be charged via line 12 to incubator 10. As will be apparent to those skilled in the art, because such genes are so prevalent in virtually all organisms which have contact with air, any of such organisms may be used.

By way of illustration, and not limitation, one may use yeast cells such as, e.g. Saccharomyces cerevisiae RSY6, which is described in U.S. Pat. No. 4,997,757; the disclosure of this United States patent is hereby incorporated by reference into this specification. By way of further illustration, one also may use strain SC288C of Saccharomyces cerevisiae yeast which may be obtained from the Yeast Genetics Stock Center of Berkeley, Calif.

The catalase enzyme also is present in most aerobic organisms. As is known to those skilled in the art, catalase is that hemoprotein enzyme that catalyzes the decomposition of hydrogen peroxide to oxygen and water. It is commonly identified in the International Enzyme registry as EC 1.11.1.6. This enzyme is well known to those skilled in the art and is described, e.g., in U.S. Pat. Nos. 5,080,886, 3,523,871, 5,010,007, 4,065,357, 3,926,732, and the like. The disclosure of each of these United States patents is hereby incorporated by reference into this specification.

By way of further illustration, bacterial catalase genes are discussed in an article by J. Switala et al. entitled "Homology among bacterial catalase genes," published in the Canadian Journal of Microbiology, 36(10):728–32 (October, 1990). Furthermore, one of the two catalase genes in yeast (the CTA1 gene) is described in an article by G. Cohen et al. entitled "Sequence of the . . . CTA1 gene . . . " which was published in the European Journal of Biochemistry, 17691):159–163 (September, 1988). The other of the two catalase genes in yeast (the CTT1 gene) is described, e.g., in an article by Walter Spevak et al., entitled "Isolation of the Catalase T Structural Gene . . . " which was published in Molecular and Cellular Biology, Volume 3, No. 9,. 1545–1551 (1983).

By way of yet further illustration, a plant catalase is described in an article by W. Ni et al. entitled "Characterization of a cDNA encoding cottonseed catalase" which was published in Biochmicia Et Biophysica Acta, 1049 (2):219–22 (June, 1990). A mammalian cell catalase was described in an article by H. Nakashima et al. in an article entitled "Isolation and Characterization of the rate catalase encoding gene," which was published in Gene, 79(2):279–288 (July, 1989).

Referring again to FIG. 1, the cell material in incubator unit 10 is incubated in the presence of media to cause the cells to grow. One may use any suitable media such as, e.g., YEPD media when yeast cells are to be incubated.

As is known to those skilled in the art, YEPD medium contains yeast extract (one percent, by weight), peptone (any of various protein compounds obtained by acid or enzyme hydrolysis of natural protein, which is present in a concentration of 2 percent, by weight), dextrose (2.0 percent by weight), agar (2 percent by weight), and water.

In another preferred embodiment, one may use "synthetic complete medium". Synthetic complete medium contains yeast nitrogen base without amino acids and with ammonium sulfate, (0.67 percent, by weight, which can be purchased from Difco Laboratories of Detroit, Mich.), dextrose (2 weight percent), agar (2 weight percent), water, and the following amino acids and bases per liter of total solution: 20 milligrams each of L tryptophan, L histidine hydrochloride, L arginine hydrochloride, L methionine, L isoleucine, L tyrosine, L lysine hydrochloride, adenine sulfate, and uracil; 30 milligrams per liter of total solution of L leucine; 350 milligrams of L threonine per liter of solution; and 75 milligrams per liter of L valine.

Other suitable growth media can also be used. Thus omissions, and/or additions may be made in the concentrations and/or the compositions of the media described above without adversely affecting their performance.

After a suitably large cell culture has been incubated, the superoxide dismutase gene and the catalase gene are both isolated from the cell culture by conventional means. The cell culture is charged via line 14 to isolation member(s) 16. As will be apparent to those skilled in the art, more than one process step and more than one device often is required for the isolation and modification of the gene.

Those skilled in the art are well aware of the protocols used in such isolation. Thus, by way of illustration, in Frederick M. Ausubel et al.'s "Short Protocols in Molecular Biology," Second Edition (John Wiley & Sons, New York, 1992) the construction of recombinant DNA libraries is described in Chapter 5 (at pages 5–4 to 5–20), and the screening of these libraries is described in Chapter 6 (at pages 6–3 to 6–14). Thus, for example, in Bernard Perbal's "A Practical Guide to Molecular Cloning," Second Edition (John Wiley & Sons, New York, 1988), the preparation of genomic libraries is described in chapter 17 (pages 480–516), and the cloning of cDNA species is described in chapter 19 (at pages 550–578). Thus, by means of further illustration, European Patent Application 84111416.8, published Apr. 24, 1985 under no. 0138111, discloses the cloning and sequencing of the human SOD cDNA and the production of the human SOD in bacteria and yeast. The disclosure of this European Patent Application is hereby incorporated by reference into this specification.

The DNA genes coding for superoxide dismutase and for catalase are either charged via line 18 to gene modification unit 20 or via line 22 to incorporation unit 24. If the genes isolated in isolation unit 16 do not contain appropriate regulatory signaling means for their expression in the host, then they must be modified so that these signals are incorporated into them. If, on the other hand, they do contain appropriate regulatory signaling means, they may be directly incorporated into the vector in incorporation unit 25 via line 24.

Thus, by way of illustration and not limitation, when the superoxide dismutase gene or the catalase gene is isolated from, e.g., human cells, these genes do not contain sequences which will cause their expression in yeast, or other fungi. Thus, if they are to be expressed in, e.g., yeast, they must be suitably modified.

This modification is usually required when one deals with any genes to be expressed in foreign cells. However, even when a gene is to be expressed in the same organism from which it was derived, it often is desirable to modify it so that its expression in such organism is facilitated Those skilled in the art are aware of how to modify various genes so that, e.g., their expression in yeast can be facilitated and regulated. Such expression signals are well known and are described, e.g., in U.S. Pat. Nos. 4,990,446, 4,945,046, 4,855,231, 4,615,974, 5,096,825, 5,089,395, 5,045,463, 4,837,147, 4,806,472, and 4,745,057. The entire disclosure of each of these patents is hereby incorporated by reference into this specification.

By way of further illustration, the modification of genes to facilitate their expression in yeast is described in a book by C. Guthrie et al. entitled "Guide to Yeast Genetics and Molecular Biology" (Academic Press, Inc., New York, 1991), at pages 373–397.

In one embodiment, the superoxide dismutase gene from human cells is modified by adding to it on its 5' end a promoter, such as the promoter from the alcohol dehydrogenase 1 yeast gene (ADH1). In one embodiment, the SOD gene is further modified by adding to its 3' end a transcriptional terminator, such as the transcriptional terminator from the from the yeast TRP1 gene. The ADH1 promoter may be obtained from the plasmids listed on page 383 of the aforementioned Guthrie book such as, e.g., plasmid pAAH5. The TRP1 terminator is described on page 383 of the Guthrie book.

In one embodiment, illustrated in FIG. 1, one need not go through the incubation and isolation steps in the case of genes which already have been isolated by other researchers. If such gene(s) requires modification, as described above, they may be charged via line 26 to the gene modification unit 20. If, on the other hand, the gene does not require modification, it may be charged directly to the incorporation unit 25 via line 23.

Those skilled in the art are aware of the fact that the superoxide dismutase gene and the catalase gene may be obtained from more than 30 different laboratory sources. Thus, the preparation of manganese superoxide dismutase was described in an article by S. L. Church (of the Department of Pediatrics, St. Louis Children's Hospital, Washington University School of Medicine, St. Louis, Mo. 63110) entitled "Manganese superoxide dismutase: nucleotide and deduced amino acid sequence of a cDNA encoding a new human transcript," which was published in the Journal Biochimica Et Biophysica Acta, 1087(2):250–2 (Oct. 23, 1990).

Thus, by way of further illustration, the Cu.ZnSOD gene (SOD1) of Saccharomyces cerevisiae, was cloned in a vector called pYEp352 plasmid to yield vector p352-2.05. This work was done, for example, by O. Bermingham-McDonogh et al. in J. S. Valentine's laboratory at the University of California at Los Angeles; and the gene was obtained by applicants from E. B. Gralla of this laboratory. This work was described in an article by O. Bermingham-McDonogh entitled "The copper, zinc superoxide dismutase gene of Saccharomyces cerevisiae: cloning, sequencing, and biological activity," Proceedings of the National Academy of Sciences U.S., 85, pages 4789–4793 (1988).

As is known to those skilled in the art, the vector pYEp352 is generally available to the scientific community and is described in a review article by S. A. Parent et al. appearing in "Yeast," volume 1, page 83 (1985).

By way of further illustration, one may obtain a manganese containing SOD gene from Y. S. Ho and J. D. Crapo of the Department of Medicine, Duke University Medical Center, Durham, N.C. 27710. The preparation of these genes was disclosed in an article by Dr. Ho et al. entitled "Isolation and Characterization of Complementary DNA's encoding human manganese containing superoxide dismutase," which was published in Federation of European Biochemical Society Letters, 229(2):256–260 (1988).

Those skilled in the art are well aware of many other sources of the superoxide dismutase gene. The catalase genes are also freely available within the scientific community; see, e.g., the sources of such gene described elsewhere in this specification.

Either the modified gene (charged via line 22) or the unmodified gene (charged via line 23 or 24) is incorporated into a vector which will be capable of entering and replicating within the living fungal cells to be modified.

As is known to those skilled in the art, a fungus is a eukaryotic organism that may be unicellular or made up of filaments and which lacks chlorophyll. By way of illustration, suitable fungi which may be used in the applicant's process include yeast and other ascomycete fungi, eumycota fungi, myxomyceta fungi, and the like; see, e.g., the definitions of these terms in W. G. Hale et al.'s "The Harper Collins Dictionary of Biology (Harper Collins Publishers (New York, 1991).

In one preferred embodiment, the fungi used in the process of the invention are a species of yeast. As is known to those skilled in the art, yeast is a collective name for those unicellular ascomycete or basidiomycete fungi of economic importance in the brewing and baking industries. Thus, by way of illustration and not limitation, one may use the yeast genus Saccharomyces, the yeast genus Zygosaccharomyces, the yeast genus Kluyveromyces, and the like.

By way of further illustration, suitable fungi which may be used in the process of this invention are described in U.S. Pat. Nos. 5,006,471, 5,084,385, 5,081,033, 5,079,011, 5,073,489, 5,010,182, 4,973,560, 4,894,338,4,885,176, 4,859,596, 4,842,869, 4,957,862, 4,954,440,4,935,349, 4,870,011, 4,803,800, 4,731,248, and 4,486,533. The disclosure of each of these patents is hereby incorporated by reference into this specification.

In one preferred embodiment, the process of this invention utilizes those viable fungal species, e.g. Saccharomyces cerevisiae, which can be transformed with DNA, or are amenable to induced mutagenesis. Thus, by way of illustration, such species of yeast may contain a deletion or stable mutations of the URA3, or the LEU2, TRP1, LYS2, ADE2 or any other gene that can complement a growth limiting mutation.

By way of further illustration, one may use yeast strains S288C and A364A, both of which are obtainable from the Yeast Genetics Stock Center of Berkeley, Calif.

Some of the yeast vectors which may be used are described on pages 13–19 to 13–27 of Ausubel's book. Thus, by way of illustration, and referring to such book, one may use YEp vectors (such as YEp13, YEp24, YEp52, YEplac112, YEplac181, YEplac195, and the like), YRp vectors (such YRp7, YRp17, and the like), integrated YIp vectors (such YIp5), the extended series of YRp, YEp, and YCp plasmids described on page 13–21 of the Ausubel book, and the like. These type of yeast vectors are commercially available and may be obtained, e.g., the Invitrogen Inc., Clontech Corporation, and the like. The addresses and telephone numbers of these and similar companies are presented in Appendix 4 of the Ausubel book as well as in the Biotechnology Directory cited at page A4–1 of said book. Furthermore, these and similar vectors are also described in the aforementioned Guthrie book, at pages 195–230.

By way of further illustration, one may use standard yeast multicopy vectors. Thus, for example, standard yeast multicopy vectors (YEp) can be used for the introduction of the catalase T gene into yeast cells (see Methods in Enzymology, Vol 194, Guthrie C, Fink G R (eds) 1991, Guide to Yeast Genetics and Molecular Biology). YEp (yeast episomal plasmid) vectors carry a gene whose presence can be selected in yeast (marker gene) as well as a sequence that promotes autonomous replication in yeast. In addition, all vectors contain bacterial sequences that allow selection and propagation in E. coli. The yeast selectable markers used are cloned yeast genes for which strains containing non revertible mutations of that gene are readily available, e.g. the LEU2 or the URA3 gene.

Also one may use plasmids with dominant detectable markers, which allow transformation of essentially any yeast strain.

By way of illustration and not limitation, the bacterial neomycin gene can be used which confers resistance to G418 in yeast. By comparison normal yeast strains are sensitive to G418. The ability to select for the neomycin gene in yeast is described in a publication entitled "Expression of a transposable antibiotic resistance element in Saccharomyces" by Jimenez et al. (1980) published in Nature 287 on pages 689 to 691. By way of further illustration, another gene useful for this embodiment is the hygromycin B gene which produces resistance to hygromycin B in yeast. By comparison normal yeast strains which do not contain the hygromycin B resistance gene are unable to grow in the presence of 200 microgram of hygromycin B per milliliter of growth medium. The usefulness of the hygromycin B gene in yeast is described in a publication entitled "Hygromycin B resistance as dominant selectable marker in yeast" by Kaster et al. (1984) published in Current Genetics, Volume 8 on pages 353 to 358.

In one embodiment, for the overexpression of SOD, one may use a particular class of high copy number vectors (such as, e.g., pJDB207) that is maintained in cells with a very high copy number (see, e.g., J. D. Beggs, Alfred Benzon Symp. 16, p383, 1981; J R Broach: "Construction of high copy yeast vectors using 2 micrometer circle sequences", p307–325, in Methods of Enzymology 101, eds. S. P. Colowick, N O Kaplan, 1983). By way of illustration, pJDB207 is a derivative of the more common plasmid pJDB219, which is described in the aforementioned Broach article. It contains the region spanning the LEU2 gene and the origin of replication from pJDB219 cloned into the bacterial vector pAT153. The basis for the high copy number is a LEU2 allele (leu2-d) which complements a leucine auxotrophy poorly. As will be apparent to those skilled in the art, there are other vectors which work in similar manners.

Other yeast expression vectors are described in U.S. Pat. such as, e.g., U.S. Pat. Nos. 4,990,446, 4,945,046, 4,855,231, 4,615,974, 5,096,825, 5,089,395, 5,045,463, 4,837,147, 4,806,472, and 4,745,057. The entire disclosure of each of these patents is hereby incorporated by reference into this specification.

Other vectors which may be used with yeast will be readily available to those skilled in the art. Thus, e.g., one may use artificial yeast chromosomes, such as those described on pages 251–273 of the Guthrie book.

Referring again to FIG. 1, both the superoxide dismutase gene and the catalase gene may be incorporated into the same vector. Alternatively, these genes may be incorporated into different vectors. One or more vectors may be utilized which incorporate one or both of the genes into the chromosome of the host cell and/or introduce such genes extra-chromosomally.

Means for incorporating the gene(s) into the vector(s) are well known to those skilled in the art. Thus, for example, one may use the conventional methods for the insertion of genes into vectors disclosed at column 10 of U.S. Pat. No. 4,742,004 and the references cited therein; the disclosure of this patent is hereby incorporated by reference into this specification.

The modified vector is then charged via line 28 to transformation unit 30, wherein it is used to transform competent fungal cells, such as appropriately treated living yeast cells. Those skilled in the art are well aware of how to treat such yeast cells in order to have them be transformed with a vector.

In one preferred embodiment, two separate plasmids, each one containing either the cloned superoxide dismutase gene or the cloned catalase gene, are both mixed with a solution containing the yeast cells, and the mixture so formed is incubated. One preferred aspect of this transformation procedure is described below in detail.

By way of illustration and not limitation, one can use the "High efficiency transformation method of intact yeast cells using single stranded nucleic acids as carrier" disclosed by R. Schiestl and D. Gietz in an article published in Current Genetics 1989 volume 16 on pages 339 to 346 or any further development thereof such as the ones published by Gietz and Schiestl 1991 in Yeast volume 7 on pages 253 to 263 or the one published by Gietz et al. 1992 in Nucleic Acids Research volume 20 on page 1425, or another method of transformation by electropotation published by Becker and Guarente 1991 in Methods in Enzymology, volume 194 on pages 182 to 186. In one experiment, 300 milliliters of a culture of strain DBY747 (obtained from Dr. David Botstein of Stanford University, Palo Alto, Calif.) in YEPD medium was grown overnight to 5 to $7 \times 10^6$ cells per milliliter from a fresh overnight culture. Cells were collected by centrifugation at 5,000 r.p.m. for 5 minutes in a GSA rotor in a Sorvall centrifuge. The cells were resuspended in 1.5 milliliters of a solution of Tris/EDTA, pH 7.5 (hereinafter called TE) and 0.1 molar lithium acetate (obtained from Sigma Chemical Company of St. Louis, Mo. 63178). Five micrograms of the plasmids were mixed with 200 micrograms of sonicated salmon sperm carrier DNA (20 microliters of a solution of denatured salmon sperm DNA [10 milligrams/milliliters], obtained from Sigma Chemical Company, dissolved in TE buffer, sonicated with a MSE 150 Watt Ultrasonic Disintegrator (obtained from Measuring and Scientific Equipment Ltd. Manor Royal, Crawley, Great Britain) for 10 minutes, extracted once with an equal volume of phenol, precipitated with twice the volume of ethanol, dried under vacuum produced by a water pump, and redissolved in TE buffer in an Eppendorf tube; and 0.2 milliliters of the cell suspension was added to the DNA. The suspension was incubated for 30 minutes at 30 degrees celsius with agitation in a New Brunswick controlled environment shaker. Thereafter 1.2 milliliters of a solution containing 40% polyethylene glycol 4000 (obtained from Sigma Chemical Company), TE buffer with a pH of 7.5 and 0.1 molar lithium acetate was added, and the solution was gently mixed. The solution was incubated for another 30 minutes at 30 degrees celsius with agitation and thereafter heated for 7 minutes in a 42 degrees celsius water bath. The cells were then collected by centrifugation in a Fisher microfuge for 5 seconds, washed twice with TE buffer with a pH of 7.5, and finally resuspended in one milliliter of TE buffer. 0.2 milliliters of this cell suspension was plated onto one petri dish containing medium lacking uracil.

By way of further illustration, yeast transformation also is illustrated in U.S. Pat. No. 4,997,757, the disclosure of which is hereby incorporated by reference into this specification.

It will be apparent to those skilled in the art that other means of transforming the yeast may be used. Thus, e.g., one may use an electroporation process utilizing particle guns, one may use conjugation with bacteria, and the like. These and other conventional transformation processes are within the scope of the applicants invention.

The living, transformed yeast cells are then charged via line 32 to selection unit 34. In this step of the process, the cells are exposed to selection medium compatible with the selection markers in the vector(s), thereby only allowing those cells which have been transformed to grow. Inasmuch as there will preferably be a separate selection marker for each of the superoxide dismutase and the catalase gene containing plasmids, only those transformed yeast cells which contain both the additional superoxide dismutase and catalase plasmids will be selected.

A selection medium is preferably selected for the yeast strain which, after the yeast cells have been plated onto it and grown, enables one to identify those yeast cells which have taken up and replicate the plasmids. Those skilled in the art are aware of many such growth media which facilitate the identification of such yeast cells.

By way of illustration and not limitation, many such media are described in F. Sherman et al.'s "Methods in yeast genetics, a laboratory manual" (Cold Spring Harbor Laboratory, Cold Spring Harbor, N.Y., 1986).

As those skilled in the art are aware, each construct requires a certain selection medium which will enable one to identify the cells which have taken up DNA. Thus, one can use uracil omission medium (medium lacking uracil) for a construct utilizing one gene in the uracil metabolic pathway for insertion etc. Thus, for example, uracil may be omitted from the synthetic complete medium described elsewhere in this specification to provide a medium which contains all growth factors except uracil. Likewise, for these constructs, one can use leucine omission medium for a construct utilizing one of the genes in the leucine metabolic pathway. Furthermore, combinations of the above mentioned media can be used for the selection of cells that will maintain two plasmids with different marker genes, e.g. one gene from the uracil metabolic pathway, and one gene from the leucine metabolic pathway.

Those transformed yeast cells which are selected for may be cultured in growth unit 37 and thereafter passed via line 36 to assay unit 38, wherein the concentrations of active catalase enzyme and active superoxide dismutase enzyme in the transformed cells may be determined.

The concentration of active catalase enzyme in the transformed cells may be determined by conventional means. Thus, e.g., the preparation of cell extracts and the spectrophotometric measurement of total catalase activities (by following the disappearance of hydrogen peroxide at 240 nm) may be carried out in accordance with the procedure described in an article by R. F. Beers et al. appearing in the Journal of Biological Chemistry 195 (1952). One may also use the procedure described in a paper by P. H. Bissinger et al. entitled "Control of Saccharomyces cerevisiae catalase T gene (CCT1) by nutrient supply via the RAS-cyclic AMP pathway", published in the Journal of Molecular and Cellular Biology, volume 9(3), pages 1309–1315 (1989).

Protein concentration of extracts may be assayed by the method of Bradford M M.,1976, Anal. Biochem 72, 248–254.

The specific activity of the total cellular superoxide dismutase may be determined in unit 38 by a process utilizing the oxidation of nitroblue tetrazolium, NBT, which may be obtained as reagent number N6876 from the Sigma Chemical Company of St. Louis, Mo. (see the 1992 catalog). Using xanthine (Sigma reagent number X0626) as a substrate and converting it to uric acid, the enzyme xanthine oxidase (Sigma reagent number X4500) generates superoxide anions ($O_2^-$). The $O_2^-$ oxidation of nitroblue tetrazolium elicits a colour change from yellow to blue. This can be measured spectrophotometrically at 560 nm. SOD catalyzes the reaction of superoxide to hydrogen peroxide and can inhibit the $O_2^-$ oxidation of NBT. Purified CuZnSOD (Sigma reagent number S5389) can be used to construct a standard curve with one unit of SOD defined as the amount of SOD that can inhibit the blue colour formation of NBT by 50%. The reaction mix (16 milliliters, for 20 reactions) consists of: Xanthine (222 microliters of 9 mM stock solution—0.157 g in 100 milliliters 0.05M buffer; NBT (500 microliters of 2.24 mM stock solution—0.183 g in 100 milliliters 0.05M buffer); diethylenetriaminepentacetic acid (1.5 milliliters of 13.3 mM stock solution of Sigma Reagent no. D6518—0.524 g in 100 milliliters 0.05M buffer); Bovine Serum Albumin (Sigma reagent number A9647)—Fraction V (260 µl of 10 milligrams/milliliters stock solution); Bathocuproinedisulfonic acid (200 microliters, of 5 mM stock solution of Sigma reagent number B1125—0.282 g in 100 milliliters); buffer to 16 milliliters final volume. All solutions are made in 0.05M Sodium Phosphate Buffer pH 7.8. SOD inhibits the formation of the blue dye. Purified commercially available SOD (Sigma reagent number S5389) can be used to construct a reference of SOD mediated inhibition of color formation.

One may, from these measurements, construct a curve showing the percent inhibition versus log of the nanograms of purified SOD. As will be apparent to those skilled in the art, the percent of inhibition is equal to: (Absorbance change/min at zero SOD—sample absorbance change/minutes) divided by (Absorbence change/minute at zero SOD).

The specific activity is determined by measuring the protein concentration (Bradford M M.,1976, Anal. Biochem 72, 248–254) and calculating the SOD units per milligram protein.

To provide a control and to generate comparative data, one may charge unmodified fungal cells which are identical to the cells used in the process prior to their transformation via 40 into assay unit 38. Furthermore, such unmodified cells may also be charged via line 42 into laboratory 44 to generative comparative data regarding the heat resistance and/or the pressure resistance of such cells.

The transformed cells selected in unit 34 are then passed via line 46 to culturing unit 37. One may use any of the conventional laboratory incubators and/or shakers in the growth process. Thus, for example, one may use the Precision Bench top Incubator, model number 11-6908A, illustrated on page 972 of the 1992 Fisher-Scientific catalog. Thus, e.g., one may use a New Brunswick Shaker, model number G25S, catalog number 14-278-65, illustrated on page 1437 of the 1992 Fisher Scientific catalog.

In general, the selected cells will be grown at a temperature of from about 12 to about 37 degrees Celsius for at least about 1 hour. It is preferred to grow the cells at a temperature of from about 15 to about 30 degrees Celsius for at least about 12 hours.

As will be apparent to those skilled in the art, the growth medium used in culturing device 37 preferably will select for the presence of the transformed DNA and the growth of only the transformed cells. As will be apparent to those skilled in the art, the choice of the medium used will depend upon the type of markers present in the vector(s).

The genetic engineering methods described above are well known to those in the art. Thus, these and other yeast genetics methods are described in detail in a publication by F. Sherman et al. entitled "Methods in yeast genetics, a laboratory manual" (Cold Spring Harbor Laboratory, Cold Spring Harbor, N.Y., 1986). Reference may also be had to the Guthrie et al. book referred to elsewhere in this specification. Thus, the medium used can lack an ingredient essential for growth which is present to the desired extent only in the fully transformed cells. Thus, a medium can be used comprised of one or more antibiotics and/or metals which will tend to kill those cells which do not contain plasmids with dominant selectable markers, such as antibiotic resistance and/or metal resistance. See, e.g., U.S. Pat. No. 4,511,652.

In one embodiment, where the superoxide dismutase gene and the catalase gene have been integrated into the genome of the yeast cells, it is not necessary to use growth media which selects for the presence of the plasmids.

In one preferred embodiment, at least about 1,000 parts per million of a cation is added to growth unit 37. It is preferred to add at least about 10,000 parts per million of the cation. In one embodiment, from about 100 to about 600 micrograms of the cation are added per milliliter of the mixture in the growth unit.

In another embodiment, at least about 10 parts per million of the cation are added to the system.

As is known to those skilled in the art, there are three known forms of superoxide dismutase, each with a separate metal ligand; see, e.g., U.S. Pat. No. 4,742,004, the disclosure of which is hereby incorporated by reference into this specification. These forms of SOD contain different metals bound to the protein molecules, namely iron, manganese, or both copper and zinc.

In one form of SOD, referred to as manganese SOD, manganese is the metal ligand. This form of SOD is prevalent in prokaryotes, and in the mitochondrial matrix and/or the microbodies of eurkaryotic cells.

In one aspect of applicants' process, a metal compound is added via line 46. One preferably uses the compound of that metal which is identical to the metal used as the ligand in the superoxide dismutase expressed by the gene of the cell in question. Thus, where the gene which is cloned in applicants process codes for manganese superoxide dismutase, then one adds a compound of manganese via line 37. When the gene which is cloned in applicants process codes for iron superoxide dismutase, one may add a compound of iron. When the gene which is expressed codes for Cu,Zn-superoxide dismutase, one may add a compound of copper and/or zinc.

It is preferred to use either the chloride, or the sulfate of the cation(s) in question.

In one embodiment, the elemental form of the cation is added to the mixture.

In one embodiment, it is important to add the cation prior to the time the optical density of the growth culture, as measured at 600 nanometers, exceeds about 0.1. Thus, samples of the growth culture may be periodically removed via line 48 and tested in laboratory 44 to determine its optical density.

In one embodiment, a gaseous substance is introduced into the culture unit via line 50 during the growth cycle. One may, during part or all of such cycle, flush the system with an inert gas (such as nitrogen). Alternatively, or additionally, one may introduce oxygen or air into line 50 and flow it into the system.

In one embodiment, the cloned superoxide dismutase gene and/or the cloned superoxide catalase gene contains a regulatory promoter which can be turned on and/or repressed by the addition of a specified substance and/or by treatment with heat, and/or deprived of certain stimuli or nutrients. Thus, e.g., and by way of illustration, one can insert a promoter into the superoxide dismutase gene which would be turned on by the addition of copper ion (metallothionein) which is encoded by the Cup1 locus. Such a promoter may be incorporated into the yeast by the process illustrated in U.S. Pat. No. 4,511,652, the disclosure of which is hereby incorporated by reference into this specification.

The heat resistance of cells grown in unit 37 may be determined in laboratory 44. Beat resistance is defined as a significant increase in the inheritable tolerance of exposure to high temperatures (25° C.–95° C.). A typical exposure to heat would be a 30 minute heat shock at 50° C. Alternatively, or additionally, one may expose the yeast to other heat shock regimens such as, e.g., at least 60 minutes at 40 degrees Celsius. As will be apparent to those skilled in the art, heat shock in the yeast may also be induced by rapidly raising the temperature of the yeast from, e.g., 23 to 37 degrees Celsius.

One may determine heat resistance by conventional means. Thus, e.g., in one embodiment, to test resistance of cells under a "lethal heat shock" regime, yeast cultures were grown at 23° C. to an optical density at 600 nm of 1. The cultures were divided, and one half of each culture was subjected to heat shock (50° C. for 20 min), and heat shocked and non heat shocked cells were plated on YEPD medium after serial dilutions to assay for survivors. The percentage of survivors in the treated culture is compared with the percentage of survivors in the untreated culture.

The heat resistance characteristics of cells with differing activities of superoxide dismutase and of catalase can thus be evaluated in applicants' process.

It is preferred that the superoxide dismutase activity of the cloned yeast genes be at least about 1.2 times as great as the superoxide dismutase activity of the unmodified yeast genes. It is more preferred that the SOD activity of the cloned yeast be from about 1.2 to about 20 times as great as the SOD activity of the unmodified yeast.

It is preferred that the catalase activity of the modified yeast be at least about 1.5 times as great as the catalase activity of the unmodified yeast. It is more preferred that the modified yeast have a catalase activity of from about 1.5 to about to about 100 times as great as the unmodified yeast.

The combination of the increase in both the SOD activity and the catalase activity produces an unexpected, beneficial increase in yeast survival. Without either of the components, the high concentration of the other component often results in a detrimental effect upon the performance of the yeast under stress conditions. The presence of both components, however, substantially increases the survival rate of the yeast cells under extremes of temperature.

Although applicants prefer to provide a modified yeast with both additional superoxide dismutase and catalase genes, one does sometimes achieve improved results in the case where the modified yeast only contains additional catalase or superoxide dismutase genes. However, the presence of both of these genes often produces a substantially greater synergistic improvement than one would expect from the results of using either gene alone.

Modifying the Indigenous Genes of Fungal Cells

In one preferred embodiment, instead of modifying the genes of the fungal cells by the recombinant DNA techniques described above, one may modify the yeast genome in vivo by either classical mutagenesis techniques or by transformation of the yeast directly with synthetic oligonucleotides. These, and similar techniques, are well known to those skilled in the art and are described in the aforementioned C. Guthrie book. Thus, at pages 273–281 of such book, there are described classical mutagenesis techniques. At pages 362–373 are described modification methods for directly modifying yeast in vivo with synthetic nucleic acids.

Addition of Mimetic Compounds to the Yeast

In another embodiment, mimetic compounds are added to the yeast. As is known to those skilled in the art, a mimetic compound is one that simulates the effect of another compound. Thus, a antioxidant compound which removes superoxide ion (as does SOD) is a mimetic of SOD. Thus, an antioxidant compound which breaks down hydrogen peroxide radicals is a mimetic of catalase. Mimetic compounds which mimic the combined actions of SOD and catalase are also available and may be used.

By way of illustration, one may utilize mimetic compounds that react with unstable free radicals (such as, e.g., 5-dimethyl-1-pyrroline-N-oxide, Sigma reagent number D5766; 2-methyl-2-nitroso-propane, Sigma reagent number M8516, N-t-butyl-alpha-phenylnitrone, Sigma reagent number B6723, and the like), antioxidants, and the like. These compounds may be added, e.g., via line 46 prior to or during the growth cycle. Alternatively, or additionally, one may add these compounds to the unmodified yeast.

Antioxidant materials which may be added to the yeast include, e.g., thiolactate, 2-mercaptoethanesulfonic acid, N-acetylcysteine, DL-pencillamine, tocopherol, citric acid, organogermanium compounds, and the antioxidants described in U.S. Pat. Nos. 5,102,659, 5,084,482, 5,084,293, 5,075,179, 5,075,110, 5,071,873, and the like.

Construction of Plasmid pJFD101

Those skilled in the art are well aware of how to digest plasmids with restriction enzymes and to isolate the fragments so digested. Thus, by way of illustration and not limitation, one may refer to a publication by T. Maniatis et al. entitled "Molecular Cloning: A Laboratory Manual", (Cold Spring Harbor Laboratory, Cold Spring Harbor, N.Y., 1982), or Ausubel F. M. et al., "Current protocols in molecular biology", (John Wiley and Sons, 1987). In the Maniatis Laboratory Manual, restriction enzymes are disclosed in chapter 1.85, and the isolation of gene fragments by Gel Electrophoresis, if needed, is described in chapter 6.22.

A novel plasmid, identified as pJFD101, was constructed by isolating a HindIII-BamHI restriction fragment carrying the yeast catalase T gene (CTT1) from the plasmid Yep13-7308 (described in: Spevak W. et al., 1983, Molecular and Cellular Biology, 3 (9), p1545–1551), and ligating it to the general purpose yeast vector pYeplac195 (Gietz R D, Sugkind A, 1988, Gene 74, 527); the construction and use of plasmid YEplac195 is very well documented in a publication by D. Gietz and Sugkind A, 1988 published in Gene 74 on pages 527 to 534.

All of the plasmids of the YEp, YIp or YCp series published in the aforementioned Gietz et al. paper are useful in applicants' process as long as SOD and CAT genes can be transferred into those plasmids. Plasmid YEplac195, as well as the other useful plasmids published in the aforementioned paper by Gietz et al., are freely available to those skilled in the art from Dan Gietz at the aforementioned address.

The plasmid Yep13-7308 has been isolated from a yeast genomic library constructed by Nasmyth K A and S I Reed (1980, Proc. Natl. Acad. Sci.77: 2119–2123) in the process of cloning the CTT1 gene (Spevak W. et al., 1983, Molecular and Cellular Biology, 3 (9), p1545–1551). The catalase T structural gene of Saccharomyces cerevisiae was cloned by functional complementation of a mutation causing specific lack of the enzyme (ctt1). Catalase T-deficient mutants were obtained by UV mutagenesis of an S. cerevisiae strain bearing the cas1 mutation, which causes insensitivity of catalase T to glucose repression. Since the second catalase protein of S. cerevisiae, catalase A, is completely repressed on 10% glucose, catalase T deficient mutant colonies could be detected under such conditions.

A ctt1 mutant was transformed with a S. cerevisiae gene library in the E. coli—yeast hybrid plasmid Yep13 (Broach J R, et al., 1979, Gene 8: 121–133). Among the catalase T positive clones, four contained DNA fragments with overlapping restriction maps. Plasmid Yep13-7308 was one of the catalase T gene containing vectors, and has been published (Spevak W. et al., 1983, Molecular and Cellular Biology, 3 (9), p1545–1551).

Yep13-7308 has been provided to applicants by H. Ruis, Institute of General Biochemistry, University of Vienna, Austria.

Plasmid Yep352-2.05

Plasmid Yep352 is known to those skilled in the art; see, e.g., the description of this plasmid elsewhere in the specification. The plasmid Yep352 may be cut with the restriction enzyme Sph1, and ligated with a 2.05 kilobase nucleotide fragment the yeast gene coding for Cu,Zn superoxide dismutase (SOD1); the SOD1 gene has been cloned and isolated, and it is available from E. B. Gralla at the University of California at Los Angeles. This information is published in the Bermingham-McDonogh paper discussed elsewhere in this specification; and it may be transformed into yeast as a multicopy vector by conventional means, and it can be maintained on a minus uracil omission medium.

The manganese SOD gene, "SOD2," also has been cloned and characterized; see, e.g., C. A. Marres et al., "Nucleotide sequence analysis of the nuclear gene coding for manganese superoxide dismutase . . . ", European Journal of Biochemistry, 147:153–161(1985). This gene also may be incorporated into the plasmid in either a modified or unmodified form.

Plasmid pJFD102

Plasmid pJFD102 was constructed by isolating a SphI restriction fragment carrying the complete yeast CuZn superoxide dismutase gene (SOD1). The S. cerevisiae CuZn-SOD gene (SOD1) was kindly donated by Edith Gralla. A 2.05 kb SphI fragment containing the complete gene was initially cloned into the Sph1 cloning site of the multiple copy plasmid YEP352E (described by J. E. Hill et al Yeast 1, 1986). It was recloned into the Sph1 site of the multiple copy plasmid Yeplac195 to form the plasmid pJFD102.

Plasmid pJFD201

A plasmid was constructed in which both genes CTT1 and SOD1 were incorporated into the same general purpose yeast vector (YEplac195 as described previously). Plasmid pJFD201 was constructed by subcloning the HindIII/BamHI CTT1 fragment obtained from the pJFD101 plasmid into the yeast shuttle vector pRS406 (obtained from Stratgene) at the unique HindIII/BamHI site. The CTT1 gene was released by restriction digest with the enzymes SalI/SpeI. This was to enable plasmid pJFD102 to be opened at the multiple cloning site by restriction with XbaI/SalI enabling insertion of the CTT1 gene into the pJFD102 plasmid without disturbing the SOD1 gene.

Plasmid pJFD103

A fourth plasmid pJFD103 was constructed in which a HindIII-EagI fragment consisting of the yeast alcohol dehydrogenase 1 gene (ADH1) promoter sequences Described by J. L. Bennetzen and B. D. Hall in the Journal of Biological Chemistry 257:3017–3025 (1982), the human manganese cDNA (describe by S. L. Church, J. W. grant, E. U. Meesen and J. M. Trent entitled "Sublocalization of the superoxide dismutase (MnSOD(SOD2) to 6Q25 by fluorescence in situ hibridisation", Genomics 14, 823–825 1992) and terminated by the yeast alcohol dehydrogenase II (ADHII) terminator sequences (described by T. Young, V. Williamsom A. Taguchi, M. Smith, A. Sledziewski, D. Russell, J. Osterman, C. Denis, D. Cox and D. R. Beier in a publication entitled "The alcohol dehydrogenase genes of the yeast Sacchromyces cerevisiae: Isolation, structure and regulation." Basic Life Sciences, 19, 335–361 (1982)). The p490A construct consists of a 2.3 kb BamHI/HindIII fragment composed of 1.4 kb of ADH1 promoter, 0.6 kb XhoI/EcoRI section containing the human-MnSOD coding region and 0.3 kb of ADH2 terminator sequence. The 490A construct was located in the multi-copy plasmid pJDB207 and was cloned into the general purpose yeast vector YEplac195 at the BamHI-HindIII site.

Plasmid pJFD203

A plasmid was constructed in which the plasmid p7308 was digested with the restriction enzyme HindIII as described elsewhere. The 4.4 kb fragment containing the complete yeast catalase T gene was ligated into the aforementioned pJFD103 plasmid digested by the restriction enzyme HindIII to create pJFD203.

The aforementioned novel plasmid constructions (pJFD101, pJFD102, pJFD103, pJFD201 and pJFD203) as well as the aforementioned p490A construct were transformed (by the aforementioned method) into yeast strain DBY747.

Figure 2:
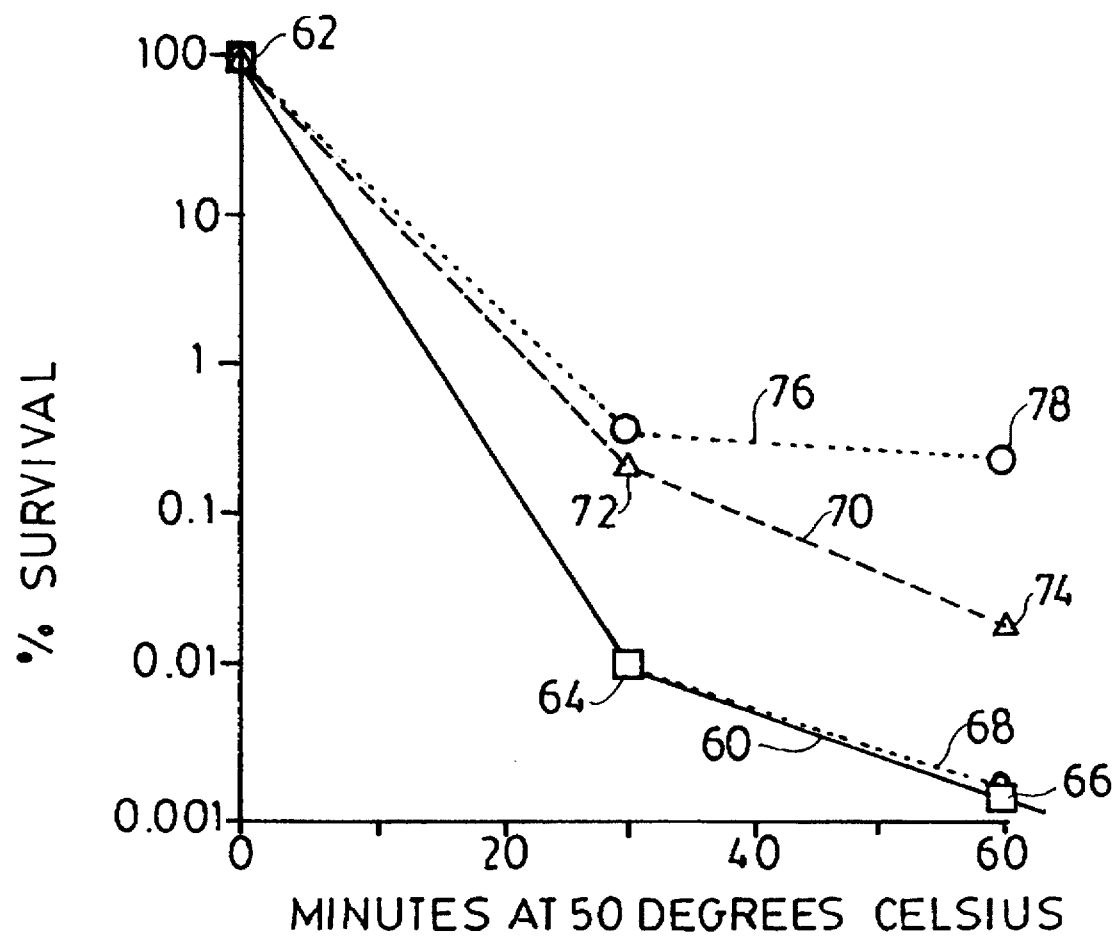
FIGS. 2, 3, and 4 are graphs showing the effects of exposure at 50 degrees Celsius upon the survival rate and the heat-induced recombination rates for yeast cells which have been transformed with several different plasmids.

Referring to FIG. 2, viability curves are shown with strains containing the aforementioned plasmid YEplac195, PJFD101, pJFD201, and p490A. Lethal heating at 50 degrees Celsius was carried out for 0, 30 and 60 minutes in a waterbath set at 50° C. as described elsewhere in this specification. Referring again to FIG. 2, line 60 denotes the viability curve for the strain containing the control plasmid YEplac195, connecting point 62, which denotes 100 percent viability as a control before heating begins, point 64 which indicates viability after 30 minutes of heating, and point 66 which indicates the viability after 60 minutes of heating. Survival curve 68 was obtained with the isogenic strain containing plasmid pJFD101 (containing the catalase gene) which does not show much of an improvement in viability. However, survival curve 70, obtained with the isogenic strain containing the aforementioned plasmid p490 (superoxide dismutase gene) shows an improvement in viability against lethal heat shock of about 20 fold at point 72 after 30 minutes of heating and at point 74 an improvement in viability of about 15 fold after 60 minutes of heating. What was equally unexpected is that if both plasmids, p490 and pJD101 were put into the same cells, a survival curve 76 was obtained showing a synergistic effect of the two plamids containing the superoxide dismutase and catalase genes. In fact, point 78 shows a level of protection from lethal heat shock of 160 fold compared to survival curve 60 of the control strain that contains only the empty vector. Since catalase alone on plasmid pJFD102 survival curve 68 did not result in an improvement of viability, the synergistic effect was unexpected. Cells of a different strain W303-1A (described elsewhere) containing pJFD203 also showed a synergistic protection of 5 fold after 60 minutes at 50 degrees Celsius.

Anaerobic Culture Conditions

Yeast cells of many strains were grown in the absence of oxygen. YEPD media supplemented with 660 milligrams/milliliters ergosterol and 6 milligrams/milliliters Tween 80 (obtained from Sigma Chemical Company) was autoclaved in air tight rubber bunged and metal cap crimped inoculation vials (Baxter). Included in the media was 0.01% resazurin (obtained from Sigma Chemical Company) which serves as an oxygen indicator being red when in the presence of oxygen and colorless when in the absence of oxygen. Vials were flushed with nitrogen gas and autoclaved.

Cells were introduced and extracted for counting via hypodermic needle injection through the rubber bungs so that at no time is the culture exposed to the oxygen present in the atmosphere. Cells were washed in degassed distilled water in an anaerobic chamber in which the usual oxygen content measured 3 parts per million and levels never exceeded 10 parts per million and pipetted into 1 milliliters aliquots containing $1 \times 10^7$ cells/milliliters. Tubes were heated at 50 degrees celsius in a water bath for time 0, and 30 minutes, diluted accordingly and plated onto solid YEPD media.

TABLE 1

Resistance of Anaerobic cells to a 50 degrees celsius Heat shock for 30 minutes

| Strain | Anaerobic (% viability) | Aerobic (% viability) |
|---|---|---|
| DBY747 | 24.23 | 0.051 |
| EG103 | 31.25 | 0.034 |
| EG110 | 41.72 | 0.002 |
| EG118 | 22.90 | 0.015 |
| W3031A | 32.37 | 0.770 |

Table 1 shows the unexpected result that anaerobic cultures are substantially more resistant to the lethal effects of a 50 degrees celsius heat exposure with at least 475×more cells surviving than aerobic cultures.

Drying of yeast cells plays an important part in food production for human consumption. For the production of bread yeast cells are dried in large containers by blowing hot air through finely distributed pellets of yeast. Thereafter, the dried yeast cells are shipped to the bakery where they are used to prepare the dough. An improved viability of the yeast cells in the drying process would be very important.

In one preferred embodiment the yeast cells are grown for the last phase of their growth cycle under anaerobic conditions. Without exposure to atmospheric oxygen the yeast cells are dried by blowing hot nitrogen through the small pellets containing yeast cells. The nitrogen gas is produced from liquid nitrogen that is purchased from a commercial source. The nitrogen gas is either reused after dehumidification or released after reutilisation of the heat content via heat exchange. The heat exchange is used to heat up new nitrogen gas. Those skilled in the art are aware that many different inert gases such as argon, etc. and a multitude of different equivalent conditions fall within the skope of this invention.

In one embodiment plasmids containing the genes catalase and/or superoxide dismutase are introduced into living animal cells, living plant cells or are incorporated into the cells of entire living animals or plants with regulatory sequences suitable for correct expression of these genes in each of these cell types.

As is known to those skilled in the art, DNA is transfected into both mammalian cells and plant cells by electroporation, viral vector mediated, cell fusion and ballistic gene insertion methods and the like and transgenic animals and plants are created by embryo microinjection, embryonic stem cells, Ti plasmids, ballistic gene insertion methods and the like.

In one embodiment, mammalian cancer cells are transfected with a vector containing superoxide dismutase and/or catalase. By way of illustration and not limitation, the method of transfection can use a vital based vector. In this situation only those cells actively dividing (as is the case for malignant tumors) are able to propagate the virus. The regulatory sequences of the catalase and superoxide dismutase genes are positioned in such a manner as to produce a messenger RNA transcribed in the reverse or antisense to the natural gene messenger RNA product. In this manner genes expression is reduced or eliminated. As is known to those skilled in the art, treatment of some cancers exploits the cancer cells sensitivity to some compounds (chemotherapy) including superoxide ion and hydrogen peroxide generators and some treatments exploit some cancers sensitivity to heat (thermotherapy) as compare to normal non cancerous cells.

Such therapies are enhanced by removal or reduction of the superoxide or catalase expression. In conjunction with localised tumor heating, mimetic antioxidant compounds can be applied to surrounding tissues (eg. N-acteyl cysteine). N-acetyl cysteine is a free radical scavenger which upon exposure to heat becomes a free radical contributor. This chemical is nontoxic in the absence of heat but becomes toxic to cells when heated. N-acetyl cysteine can be given orally or intravenously and is distributed rapidly to all tissues in the body. By applying an intense localised heat or energy source capable of producing heat on to or in the solid tumor, the N-acetyl cysteine can enhance the lethal effects of heat during thermotherapy.

As it is known to those skilled in the art, sunlight contains a certain wavelength called ultra violet light, which causes damage to human skin tissue via damage to DNA, and are also known to generate certain free radical molecules which are detoxified by catalase and superoxide dismutase. Sunlight also contains wavelengths which when incident upon the skin are absorbed and converted into heat energy. Oxygen radicals are known to those skilled in the art to be associated with aging phenomena, and excessive sunlight exposure is associated with premature aging of the skin. By way of illustration and not limitation, gene constructions containing the superoxide dismutase and catalase genes with appropriate regulatory sequences for expression in human cells could be introduced in a non permanent fashion into human skin epithelial cells or other cell types. Such introduction would be non integrative and may, although not exclusively, be facilitated via direct application of the construct, in specific lipoencapsulated vesicles, or viral vectors or other ways. Its application may be incorporated into lotion, applicator stick, balm or other means, and in conjunction with natural and artifical mimetic antioxidant compounds be employed to; protect cells from temperature, the harmful radiations from the sun, as an anti aging cosmetic and other like uses.

It is known to those skilled in the art that free radical molecules are noted to be involved in the regulation and signalling of other genes (eg. OxyR and soxRS response in bacteria, NFkB regulation in mammalian cells). Superoxide dismutase and catalase are important enzymes in the control of intracellular redox status. The intracellular redox status is manipulated via the controlled regulation of the genes superoxide dismutase and catalase. As heat has been shown to increase the flux of free radical molecules, redox status is manipulated in this way. The signalling pathways and regulatory elements sensitive to redox status is employed for direct manipulation of many gene activities.

As it is known to those skilled in the art, transgenic plants (plants genetically engineered to contain foreign genes or DNA sequences) are produced in which one or many copies of superoxide dismutase or/and catalase is incorporated into every cell of the plant or certain cells of the plant including cells contained in the fruit and seeds. In one example, fruits and seeds susceptible to the damaging processes of heat from sunlight or packaging and processing (eg. Kiwifruit) could be transformed with plasmids containing genes catalase and/or superoxide dismutase and be significantly protected from these harmful effects.

The following examples are presented to illustrate the preferred embodiments of this invention but are not to be deemed limitative thereof. Unless otherwise stated, all parts are by weight and all temperatures are in degrees centigrade Celsius.

EXAMPLE 1

In this Example, construct pJFD101 is obtained by digesting plasmid Yep13-7308 with the restriction enzymes BamHI and HindIII and by ligating the purified fragment with the HindIII-BamHI fragment from plasmid pYEplac195. The plasmids used in this example, Yep13-7308 and pYEplac195, are readily available. Thus, e.g., the pYEplac195 plasmid is disclosed by R. Gietz et al. in Gene 74, 527 (1988)

The 5.7 kilobase fragment from the pYEPlac195 plasmid and the 2.7 kilobase fragment from the Yep13-7308 plasmid were electrophoretically separated with a 0.7 percent agarose gel using a BioRad apparatus (BioRad Laboratories, Hercules, Calif.). The gel was prepared with 0.7 percent agarose (ultrapure, Sigma Chemical Company) in TBE buffer containing, per liter of distilled water, 10.8 grams of tris (hydroxymethyl)aminomethane ("Tris base"), 5.5 grams of boric acid, and 0.93 grams of disodium ethylene diamine tetraacetate dihydrate ("EDTA"). The agarose was boiled in TBE buffer until dissolved, and after it was cooled to 45 degrees Celsius it was poured into the gel tank. The solidified gel was submerged into TBE buffer, and the gel was electrophoresed with a commercially available power supply (from BioRad Laboratories) at 30 volts for 14 hours. The DNA was made visible under ultraviolet light by staining with 1 microgram per milliliter of ethidium bromide; and the desired bands were located. The DNA fragments were isolated in accordance with the procedure described by Dretzen et al. entitled "A reliable method for the recovery of DNA fragments from agarose and acrylamide gels," Analytical Biochemistry 112, pages 295–298 (1981). An incision was made with a scalpel in front of the band, and a piece of Wattman DE81 DEAE-cellulose paper (obtained from Fisher Scientific of Pittsburgh, Pa.) was inserted. The band was allowed to enter the DEAE paper by additional electrophoresis in the same direction, and thereafter the paper was removed from the gel. The paper was placed into a 0.4 milliliter Eppendorf tube, a hole was made in the bottom of the tube, and the tube was placed inside a 1.5 milliliter Eppendorf tube and spun for 15 seconds in a Eppendorf centrifuge. 0.1 milliliters of elusion buffer containing 0.2 molar sodium chloride, 50 millimolar of Tris base with of 7.6, 1 millimolar of EDTA, and 0.1 percent of sodium dodecyl sulfate was added and the elution buffer collected by centrifugation. This procedure was repeated twice, and the eluate was extracted once with an equal volume of phenol, once with a 1/1 mixture of phenol/chloroform, and once with chloroform. The solution obtained was precipitated with twice the volume of ice-cold ethanol for 30 minutes. Thereafter, the precipitate was collected by centrifugation at 10,000 r.p.m. for 5 minutes and then was washed with a 70 percent solution of ethanol, vacuum dried, and redissolved in 40 microliters of distilled water.

The fragments were then isolated from the agarose gel by a procedure described in the aforementioned Maniatis Laboratory Manual. These fragments were then ligated with DNA ligase purchased from the Bethesda Research Laboratory, of Gaithersburg, Md. The ligation procedure is well known to those skilled in the art and is described, in, e.g., pages 286 to 307 of the aforementioned Maniatis Laboratory manual. The particular ligation buffer used contained 0.66 moles of Tris base buffered to a pH of 7.5 with hydrochloric acid, 50 millimolar of magnesium chloride, 50 millimolar of dithiothreitol, and 10 millimolar of adenosine triphosphate.

The plasmid produced by this ligation, pJFD101, was used to transform E. coli strain HB101; and ampicillin resistant colonies containing the plasmid pJFD101 were isolated. The construct pJFD101 was verified by restriction analysis (see, e.g., pages 363–402 of the Maniatis Laboratory Manual). Thus, the E. coli transformation was started with an overnight culture of strain HB101 in LB medium. Strain HB101 is an E. coli K12×E. coli B hybrid that is highly transformable and commonly used for large-scale production of plasmids. HB101 has the following genotype: supE44 hsd S20($r^-_b m^-_b$) recA13 ara-14 proA2 lacY1 galK2 rpsL20 xyl-5 mtl-1. 5 milliliters of Luria Broth (LB) medium containing 10 grams of tryptone, 5 grams of yeast extract, (both ingredients obtained from Difco Laboratories of Detroit, Mich.), and 5 grams of sodium chloride per liter of medium was inoculated with a single bacterial colony and incubated overnight at 37° C. in a New Brunswick incubator with vigorous shaking. 0.3 milliliters of this culture were inoculated into 30 milliliters of fresh LB medium and incubated under vigorous shaking at 37° C. until the culture reached an optical density at 600 nanometers of 0.6. The culture was chilled by placing it onto an ice water bath and thereafter the cells were collected by centrifugation at 6,000 rounds per minute in a Sorvall centrifuge for five minutes. In the ice water bath one milliliter of an ice cold solution of 50 millimolar calcium chloride was added to the cell pellet and mixed. Ten microliters of the ligation mix was added to 5 milliliters of a solution of one molar calcium chloride, and 85 milliliters of buffer containing 10 millimolar of the aforementioned Tris-base and one millimolar EDTA were adjusted to pH 8.0 with hydrochloric acid (this buffer is hereinafter called Tris/EDTA pH 8.0). 0.2 milliliter of cell suspension was added to the DNA solution in small cooled plastic tubes. The solution was mixed gently and left on ice for 30 minutes. Thereafter the suspension was heated to 45 degrees celsius in a water bath for two minutes and then placed again into the ice bath to cool down. Three milliliters of LB medium were added and the tubes were incubated at 37 degrees celsius for two hours. Thereafter the cells were collected by centrifugation at 6,000 rpm for 5 minutes and the cell pellet suspended in 0.5 milliliters. LB medium. 0.1 milliliter were plated onto each of LB plates containing 100 micrograms per milliliter of Ampicillin (obtained from Sigma Chemical Company). Ampicillin resistant colonies were isolated and plasmid DNA was isolated from them as a modification of the boiling method, published by Holmes and Quigley in a publication entitled "A rapid boiling method for the preparation of bacterial plasmids." Anal. Biochem. 114:193–197 (1981). One milliliter of $E$ $coli$ culture containing the plasmid of interest was grown overnight in LB medium containing ampicillin. The cells were transferred to a 1.5 milliliters Eppendorf tube and spun down in a microfuge. The cells were resuspended in 0.4 milliliters of STET buffer consisting of 1 molar Tris base adjusted to pH 7.5 with hydrochloric acid, 20% triton (purchased from Sigma Chemical Company), 50% sucrose and 0.5 molar EDTA. An additional 40 milliliters of a solution containing 10 milligrams of lysozyme (purchased from the aforementioned Sigma Chemical Company) per milliliter of double distilled water was added and the solution was mixed. The solution was further boiled for 50–60 seconds and immediately thereafter placed in an ice water-bath for 1 minute. The solution was spun in a microfuge for 10 minutes at four degrees Celsius and thereafter the resulting pellet was removed with a sterile toothpick. An additional 500 milliliters of cold (−20 degrees celsius) isopropanol was added, and the contents being mixed by inverting the tube several times, and the tube was thereafter left in the freezer (−20 degrees Celsius) for 10 minutes. The solution was then spun for 3 minutes in the microfuge at four degrees Celsius and afterwards the supernatant was discarded; the pellet was resuspended in 50 milliliters of a Tris/EDTA buffer adjusted to pH 8.0 with hydrochloric acid and 50 milliliters of a solution consisting of 5 molar lithium chloride and 50 millimolar Tris/EDTA pH 8.0 was added. The contents of the tube were then mixed and incubated in an ice water-bath for 5 minutes. Thereafter, the contents were spun in a microfuge for 5 minutes at 4 degrees Celsius and the supernatant was removed and placed into a new Eppendorf tube. An additional 200 milliliters of cold ethanol (−20 degrees Celsius) was added and after mixing of the contents by inverting the tube several times the tube was left at −20 degrees Celsius for 10 minutes. After spinning of the tube for 3 minutes at 4 degrees Celsius, the precipitate was washed with one half milliliter of 80% ethanol. After another spin for 3 minutes in the microfuge at 4 degrees Celsius, the precipitate was dried in a dessicator by means of creating a vacuum with a water pump for several minutes until the precipitate was dry. Thereafter the precipitate was dissolved in 60 milliliters of double distilled water. The resulting solution contained about 2 micrograms of plasmid DNA which was then cut with restriction enzymes to determine that the isolated colonies had the correct plasmid. Thereafter plasmid pJFD101 was isolated in high yield from $E$. $coli$. 5 milliliters of LB medium with ampicillin was inoculated with a single bacterial colony, and incubated overnight at 37 degrees celsius in a New Brunswick incubator with vigorous shaking. 2.5 milliliters of the overnight culture was inoculated into a two liter flask containing 500 milliliters of M9 minimal medium (which contained per liter of distilled water solution, 6 gram of sodium phosphate ($Na_2HPO_4$), 3 gram of potassium phosphate ($KH_2PO_4$) 0.5 gram of sodium chloride (NaCl), one gram of ammonium chloride ($NH_4Cl$) and 4 grams casaminoacids [obtained from Difco Laboratories]). The medium was adjusted to a pH of 7.4, sterilized by autoclaving and after cooling the following filter sterilized solutions were added: two milliliters of one molar magnesium sulphate (milligrams$SO_4$), 10 milliliters of 20% w/v glucose, 100 milliliters. one molar calcium chloride ($CaCl_2$), and one milliliter of 100 milligrams/milliliters of Ampicillin. The culture was vigorously shaken at 37° C. until it reached an optical density at 600 nanometer of 0.6, and 65 milligrams of chloramphenicol (purchased from Sigma Chemical Company) were added; the culture was further incubated for another 14 hours in the same way. The cells were separated by centrifugation in a GSA rotor for 10 minutes at 5000 rpm in a Sorvall centrifuge. Thereafter the cells from the one liter initial culture were resuspended in 100 milliliters. TS buffer containing 10% sucrose and 0.05 molar Tris base adjusted to pH 8.0 with hydrochloric acid. The cells were again collected by centrifugation, as described above, and were chilled at 0 degree celsius in an ice-water bath and resuspended in 10 milliliters ice cold TS buffer and transferred to a 50 milliliters flask. Two milliliters of a solution of 5 milligrams/milliliters of freshly dissolved lysozyme (obtained from Sigma Chemical Comp.) were added and the solution was mixed gently on ice for 10 minutes. Four milliliters of a solution of ice cold 0.25 molar EDTA was added gently from the bottom of the flask and the mix left on ice for five minutes. 15 milliliters of triton lysis buffer (consisting of a solution in distilled water of 10% triton X-100, 0.05 molar Tris base adjusted to a pH of 8.0 with hydrochloric acid, 0.05 molar EDTA) were added and the solution was left for 10 minutes on ice. Thereafter the solution was spun in a SS34 rotor in a Sorvall centrifuge with 18,000 rpm at 4° C. for 60 minutes. The supernatant was collected and an equal volume of phenol, equilibrated with TE buffer (consisting of a solution in distilled water of 10 millimolar Tris base adjusted to a pH of 8.0 with hydrochloric acid and 1 millimolar EDTA) and an equal amount of chloroform was added. The solution was shaken for 3 minutes at room temperature and thereafter spun at 5,000 rpm in a SS34 rotor in a Sorvall centrifuge for 10 minutes; and the supernatant was collected. The same procedure, starting with the addition of phenol, was repeated a second time, and the water phases were joined; and 17.5 milligram of sodium chloride was added per milliliter of solution. Absolute ethanol was added at twice the volume of the solution, and the solution was gently mixed and left for 30 minutes in a freezer at −20° C. The solution was spun at 5,000 rpm for 5 minutes, and thereafter the pellet containing the DNA was washed with 80% ethanol. The pellet was dried and was then dissolved in 5 milliliters TE buffer. Another purification step using cesium chloride gradient centrifugation was conducted. To the TE solution, 0.75 milliliter of a buffer (consisting of one molar Tris base adjusted to a pH of 7.5 with hydrochloric acid and 0.1 milliliter of 0.5 molar EDTA in distilled water) was added. 0.978 grams of cesium chloride per (weight of solution in gram plus 1.2) was added and the volume split in half and added each into a nitrocellulose centrifuge tube of a 50 Ti rotor. 0.6 milliliters of 5 milligrams/milliliters of ethidium bromide was added to each and the solution topped up with paraffin; and the tubes were sealed. The tubes were mixed well and spun in a Beckman ultracentrifuge for 40 hours at 40.000 rpm at 20° C. The plasmid band was located using ultraviolet light and was removed with a syringe and transferred to a 30 milliliters centrifuge tube. The ethidium bromide was extracted five times with an equal volume of butan-1-ol which was saturated with TE buffer. The DNA was precipitated with three volumes of 70% ethanol in distilled water at -20° C. for one hour and collected by centrifugation at 10.000 rpm for 15 minutes in a SS34 rotor in a Sorvall centrifuge and dissolved in 0.5 milliliters TE buffer. The DNA solution was dialyzed against TE buffer for 20 hours with changes of the buffer. The optical density at 260 nanometer of the solution was determined and the concentration of DNA calculated. The yield was about 700 milligrams of plasmid DNA. Thereafter plasmid pJFD101 was transformed into DBY747, and URA+ colonies were isolated on medium lacking uracil. Transformation of yeast was carried out by treating intact cells with lithium acetate as described by Ito et al. in a publication entitled "Transformation of intact yeast cells treated with alkali cations." J. Bacteriol. 153:163–168 (1983). 300 milliliters of a culture of strain OD5 in YEPD medium was grown overnight to 5 to $7 \times 10^6$ cells per milliliter from a fresh overnight culture. Cells were collected by centrifugation at 5.000 rpm for 5 minutes in a GSA rotor in a Sorvall centrifuge. The cells were resuspended in 1.5 milliliters of a solution of Tris/ EDTA, pH 7.5 and 0.1 molar lithium acetate (obtained from Sigma Chemical) and incubated for one hour at 30 degrees celsius with constant agitation. Five micrograms of the plasmid pJFD101 was mixed with 40 microgram of sonicated salmon sperm carrier DNA (obtained from Sigma Chemical Company) dissolved in TE buffer, sonicated with a MSE 150 Watt Ultrasonic Disintegrater (obtained from Measuring and Scientific Equipment Ltd. Manor Royal, Crawley, Great Britain) for 10 minutes, extracted once with an equal volume of phenol, precipitated with twice the volume ethanol, dried under vacuum produced by a water pump, and redissolved in TE buffer in an eppendorf tube; and 0.2 milliliters of the cell suspension was added to the DNA. The suspension was incubated for 30 minutes at 30 degrees celsius with agitation (60 r.p.m.) in a New Brunswick controlled environment shaker. Thereafter 1.2 milliliters of a solution containing 40% polyethylene glycol 4000 (obtained from Sigma Chemical Company), TE buffer with a pH of 7.5 and 0.1 molar lithium acetate was added and the solution was gently mixed. The solution was incubated for another 30 minutes at 30 degrees celsius with agitation and thereafter heated for 7 minutes in a 42 degrees celsius water-bath. The cells were then collected by centrifugation in a Fisher microfuge for 5 seconds, washed twice with TE buffer with a pH of 7.5 and finally resuspended in one milliliter of TE buffer. 0.2 milliliters of this cell suspension was plated onto one petri dish containing medium lacking uracil and incubated at 30 degrees celsius for 3 days.

The yeast cells so modified exhibited substantially improved resistance to exposure to a temperature of 50 degrees Celsius for 20 minutes. When tested in accordance with the survival assay test of this specification, the mortality of the yeast was 12 times less than that of the untreated yeast cells.

The modified yeast cells were also tested to determine to what extent their catalase activity had increased. It was noted that, when the cells were tested in accordance with the procedure described in the specification, that the increase in specific catalase activity was 105 percent.

When this experiment is repeated so that the yeast cells also experience a 150 percent increase in their superoxide dismutase activity, the mortality of the modified yeast is at least 300 times less than that of the unmodified yeast.

Furthermore, plasmids pJFD102 and pJFD201 were created using the same techniques and reagents as aforementioned. pYEplac was digested with the restriction enzyme SphI as was the construct YEp352-SOD1 readily available from Edith Gralla at the University of California. The 2.05 kilobase fragment released from SphI digestion of YEp352SOD1 contains the complete gene and regulatory sequences for the yeast Cu,Zn superoxide dismutase. Isolation and purification of this fragment by the aforementioned techniques of agarose gel electrophoresis and gel purification e.g. see Dretzen et al. mentioned previously. Restriction digestion of YEPlac195 plasmid with the restriction enzyme SphI then allows ligation of the 2.05 kilobase Cu,Zn superoxide dismutase containing fragment with YEplac195 e.g. as described elsewhere in this document and being freely available to the scientific community, to create pJFD102. pJFD201 was made by ligation of the BamHI-HindIII fragment containing the yeast Catalase T gene obtained from restriction digestion of the aforementioned p7308 with BamHI/HindIII into the BamHI/HindIII site of the commercially available plasmid PRS406 from Stragene## to create PRS406-CTT1. Techniques of ligation, agarose gel electrophoresis and purification are mention elsewhere in this document. Release of the CTT1 gene was facilitated by restriction digestion of PRS406-CTT1 with restriction enzymes SalI/SpeI. pJFD102 was digested with the complementary enzymes SalI/XbaI and the CTT1 fragment ligated to form the plasmid pJFD201. The yeast cells modified with pJFD201 exhibited substantially improved resistance to exposure to a temperature of 50 degrees Celsius for 60 minutes. When tested at 50 degrees celsius for 60 minutes, the mortality of the modified yeast was 33 times less than that of the untreated yeast cells.

The construct of the human MnSOD gene was kindly provided by Walter Spevak. The p490A construct consists of a 2.3 kb BamHI/HindIII fragment composed of 1.4 kb of ADH1 promoter, 0.6 kb XhoI/EcoRI section containing the human-MnSOD coding region and 0.3 kb of ADH2 terminator sequence. The 490A construct was located in the aforementioned multi-copy plasmid pJDB207.

EXAMPLE 2

FIG. 2 shows the survival curves at time 0, 30, 60 minutes for yeast cells of the strain DBY747 MATa leu2, ura3, his3, trp1 when transformed by the aforementioned method with the aforementioned plasmids YEplac195, pJFD201, p490A and pJFD101.

Referring to FIG. 2, viability curves are shown with strains containing the aforementioned plasmids YEplac195, PJFD101, pJFD201 and p490A. Lethal heating at 50 degrees celsius was carried out for 0, 30 and 60 minutes in a water-bath set at 50° C. as described elsewhere in this specification. Referring again to FIG. 2, line 60 denotes the viability curve for the strain containing the control plasmid YEplac195, connecting point 62 which denotes 100% viability as a control before the heating occurs, point 64 which indicates the viability after 30 minutes of heating and point 66 which indicates the viability after 60 minutes of heating. Survival curve 68 was obtained with the isogenic strain containing plasmid pJFD101 (containing the catalase gene) which does not show much of an improvement in viability. However, survival curve 70, obtained with the isogenic strain containing the aforementioned plasmid p490 (superoxide dismutase gene) shows an improvement in viability against lethal heat shock of about 20 fold at point 72 after 30 minutes of heating and at point 74 an improvement in viability of about 15 fold after 60 minutes of heating. What was equally unexpected is that if both plasmids, p490 and pJD101 were put into the same cells, survival curve 76 was obtained showing a synergistic effect of the two plasmids containing the superoxide dismutase and catalase genes. In fact point 78 shows a level of protection from lethal heat shock of 160 fold compared to survival curve 60 of the control strain that contains only the empty vector. Since catalase alone on plasmid pJFD102 survival curve 68 did not result in an improvement of viability the synergistic effect was unexpected. Cells of a different strain W303-1A (described elsewhere) containing pJFD203 also showed a synergistic protection of 5 fold after 60 minutes at 50 degrees celsius.

EXAMPLE 3

Intra and interchromosomal recombination frequencies were measured during lethal heat exposure. Cells of yeast strain RS112 are freely available and described in U.S. Pat. No. 4,997,757 the disclosure of which is hereby incorporated by reference into this specification. Strain RS112 has the following genotype.

MATa ura3-52 leu2-3,112 trp5-27 arg4-3 ade2-40 ilv1-92 HIS3::pRS6 LYS2.

MATα ura3-52 leu2-D98 TRP5 ARG4 ade2-101 ilv1-92 his3D200 lys2-801) containing the his3D-3' LEU2 his3D-5" construct suitable for scoring intrachromosomal recombination events (FIG. 3) and the ade2-40/ade2-101 alleles for scoring interchromosomal recombination events (FIG. 3), was transformed with plasmids YE-plac195 (open squares) and pJFD201 (open diamonds). Transformation was performed as described in the aforementioned example. The cells were grown in SC medium lacking uracil and leucine to mid log ($5 \times 10^6$ cells/milliliters). Cells were washed in 0.87% saline and aliquots of 200 μl were prepared in thin walled 0.6 milliliter PCR tubes for each time point and placed on ice. Lethal heating was performed in a thermal cycler (Coy Tempcycler, model 110S) set at 50 degrees celsius for times 0,2,4,6,8 and 10 minutes. The aliquots were diluted accordingly with distilled water and plated onto solid synthetic complete medium (SC) and SC medium lacking histidine or adenine. Cells were allowed to grow to colonies at 30° C. for three days. Intra and interchromosomal recombination frequencies were then measured by counting the number of prototrophic colonies per viable cell as described in R. H Schiestl, R. D. Gietz, R. D. Mehta , & P. J. Hastings, in a publication entitled "Carcinogens induce intrachromosomal recombination in Yeast", *Carcinogenesis* 10,1445–1455 (1989).

To measure the effect of lethal heat-shock on genetic endpoints within the cells, the frequencies of mutation, intrachromosomal recomb nation, interchromosomal recombination were determined. The frequency mutations was measured by reversion to HIS+ of the his4-17 mutation and to ARG+ of the arg4-17 mutation in strain RS33-2C. Both of these mutations were previously used to determine mutation frequencies and our spontaneous frequencies of about $1 \times 10^{-7}$ agreed with previous data D. J Gottlieb and R. C. von Borstel, *Genetics*, 83(4) 655–666, 1976). After 10 minutes at 50° C. the frequency of reversions at both loci was increased more than 20 fold.

Figure 3:
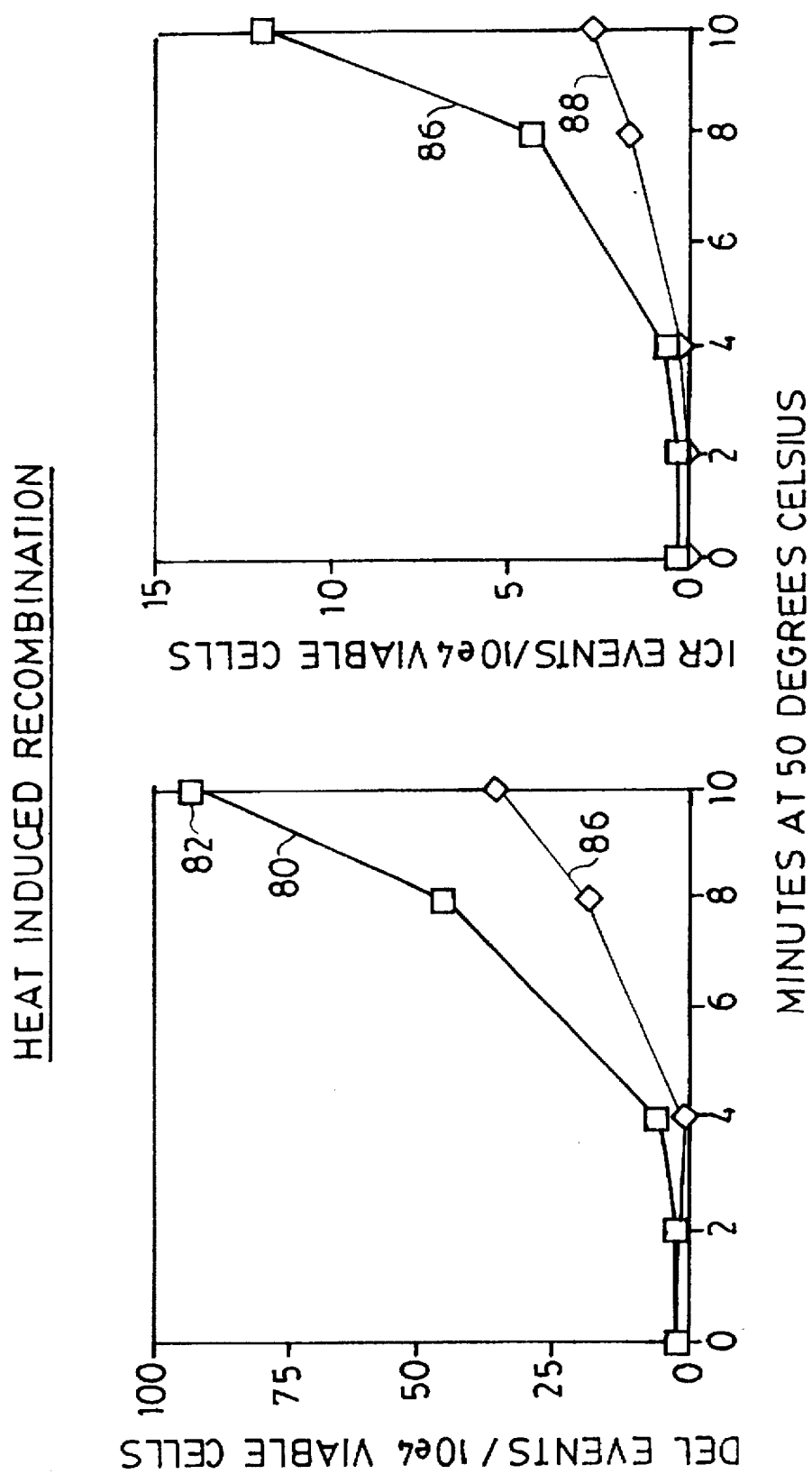

Intrachromosomal recombination was measured as recombination events between the two deletion alleles of a gene duplication at the HIS3 at the HIS3 locus, his3D-3' his3D-5' (Schiestl et al. 1988). Referring to FIG. 3 line 80 shows the recombination events induced in the control strain containing the plasmid YEplac195 by heat shock. After a ten minute lethal heat-shock the frequency of recombination was 50 fold elevated, shown as point 82. The presence of the multicopy plasmid pJFD203 containing the SOD1 gene and the CTT1 gene reduced this elevation about three fold as shown in line 84.

Interchromosomal recombination between the two homologs in diploid was measured selecting for ADE+ colonies with strain RS112 that is heterozygous for the mutations ade2-40 and ade2-101 described in the aforementioned U.S. Pat. No. 4,997,757. After a ten minute lethal heat-shock the frequency of recombination was 30 fold elevated shown as line 86 and the presence of the multicopy plasmid pJFD203 containing the SOD1 gene and the CTT1 gene reduced this elevation about five fold, shown as line 88.

EXAMPLE 4

Figure 4:
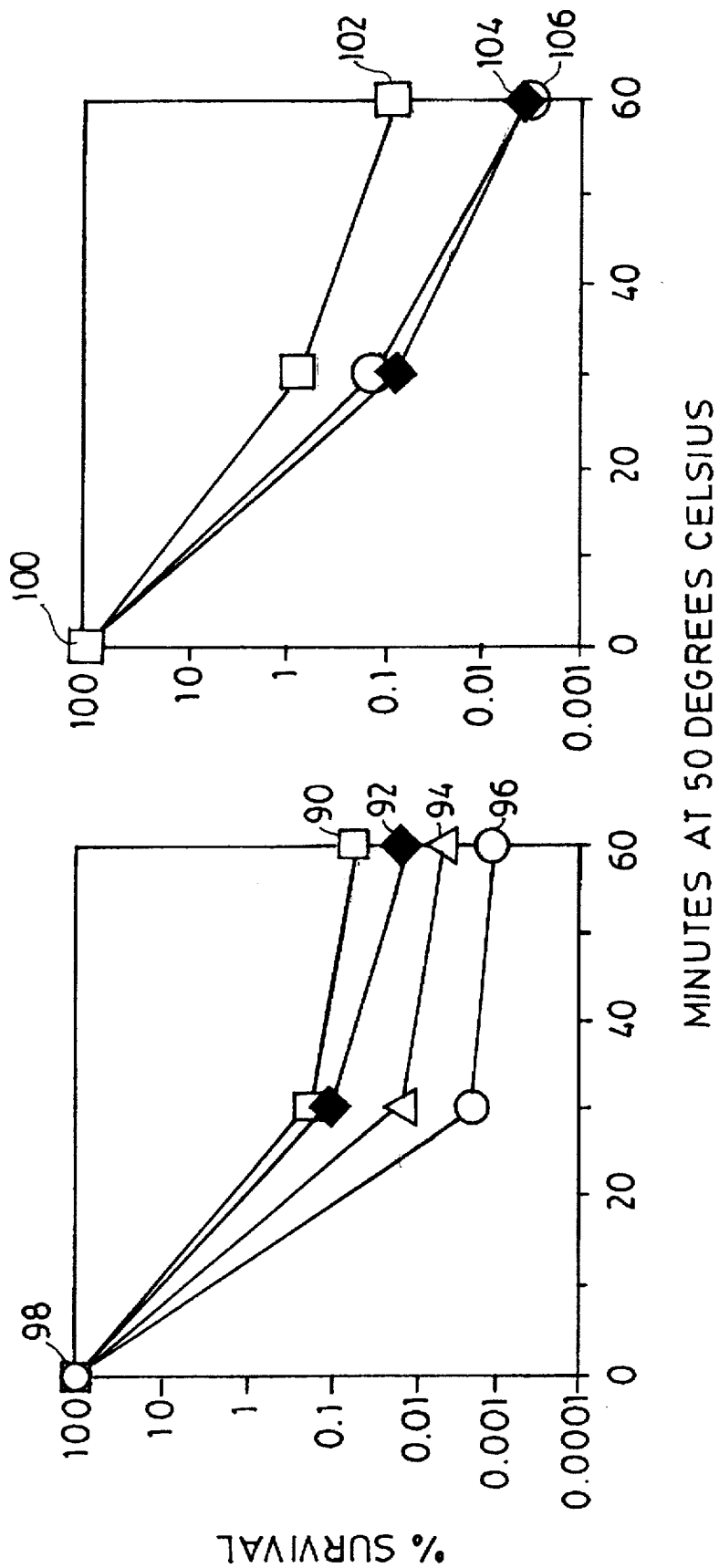

Yeast strains deficient in the antioxidant enzymes catalase CTT1 and CTA1), superoxide dismutase (SOD1 and SOD2) and cytochrome C peroxidase (CCP1) were obtained from Walter Spevak, Edith Gralla and Jim Kaput, and are freely available. Strains were grown to late log ($2 \times 10^7$ cells/ milliliters) in SC medium, washed in 0.87% saline and concentrated 2% $10^8$ cells/milliliters. Aliquots of 1 milliliters were prepared in eppendorf tubes for each time point and placed on ice. Lethal heating was performed in a water bath set at 50 degrees celsius for times 0, 30 and 60 minutes and tubes were removed at set time points and immediately placed on ice. The aliquots were then diluted accordingly and plated onto solid YPAD. Colonies were counted after 3 days of incubation at 30° C. and the percent viability was calculated with respect to cells not heated. As shown in FIG. 4 the ctt1 deletion mutant shown in line 92 is about 2 times more sensitive to the cells containing the plasmid YEplac195 (line 90) and the cta1 deletion mutant survival curve (line 94) is 10 times more sensitive to the YEplac195 curve (line 90). The double ctt1cta1 deletion (line 96) mutant shows an additive enhancement of heat sensitivity and was about 100 fold more sensitive at 30 minutes heat-shock than the wildtype.

The results for the cytochrome C peroxidase mutants are displayed in FIG. 4. The survival curves connect to line 100 which shows the 100 percent survival obtained with all strains before heating. Line 102 shows the wildtype strain containing the functional CCP1 gene and lines 104 and 106 show the 30 fold sensitization effect after lethal heating for 60 minutes in two ccp1 deletions.

The results are shown in FIG. 4 and are the means of four experiments.

EXAMPLE 5

We investigated the effect of anaerobic growth on the sensitivity of yeast to lethal heating. Cells of strain DBY747 (e.g. see elsewhere in this document) were grown to $2 \times 10^7$ cells/milliliters in YEPD. Included in the culture media was 0.01% resazurin (available from aforementioned Sigma Chemical Company) as an oxygen indicator which is red when exposed to oxygen and becomes reduced and colorless during autoclaving e.g. as described in the publication by W. Visser,W., A. Scheffers, W., H. Batenburg-van der Vegte, J. P., van Dijken, (1990) *Applied & environmental. Microbiololgy.*, 56(12): 3785–3792

Anaerobic YEPD media was prepared by autoclaving in 100 milliliters flasks stopped with rubber bungs and crimped metal cap (Baxter which were flushed with a steady stream of nitrogen. Flushing with nitrogen and inoculation was achieved via needle injection through the rubber bung. Cells were inoculated from a fermenting culture and the cultures grown over night at 30 degrees celsius. Small aliquots could be drawn from the culture flasks via hypodermic needle and syringe and the cells counted in a haemocytometer and light microscope at 250× magnfication. When the cultures had grown to $1\times10^7$ cells/milliliters they were transferred into an anaerobic chamber (Coy Laboratory Products, Ann Arbor, Mich.) where subsequent washing and aliquoting steps were undeertaken as described elsewhere in this document. Heating was performed in a water bath at 50 degrees celsius for 30 minutes in 1 milliliter eppendorf tubes. Viability at each time point was determined as aforemention and the results are displayed table 1.

It is to be understood that the aforementioned descriptions illustrative only and that changes can be made in the apparatus, in ingredients and their proportions, and in the sequence of combinat and process steps, as well as in other aspects of the invention discussed herein, without departing from the scope of the invention as defined in the following claims.

We claim:

1. A culture of dividing cells of the yeast Saccharomyces transformed with DNA encoding superoxide dismutase protein including genetic regulatory elements allowing its expression and DNA encoding catalase protein including genetic regulatory elements allowing its expression, wherein said first culture of dividing yeast cells is more heat resistant at 50 degrees Celsius for 20 minutes in the presence of oxygen containing gas than a second culture of dividing yeast cells not transformed with said DNA.

2. The transformed culture as recited in claim 1, wherein said transformed culture of dividing cells has a catalase activity of at least 1.5 times the catalase activity of cells of said culture of dividing cells not transformed with said DNA.

3. The transformed culture as recited in claim 1, wherein said transformed culture of dividing cells has a superoxide dismutase activity of at least 1.2 times as great as the superoxide dismutase activity of the cells of said culture of dividing cells not transformed with said DNA.

4. A process for preparing the transformed culture of the yeast Saccharomyces of claim 1, comprising the steps of:

(a) providing a first vector containing a gene coding for the expression of superoxide dismutase;

(b) providing a second vector containing a gene coding for the expression of catalase;

(c) incorporating said DNA coding for expression of superoxide dismutase and said DNA coding for the expression of catalase into a culture of cells, thereby providing a transformed culture of cells; and (d) growing said transformed culture of cells in a medium supplemented with a cation selected from the group consisting of the cations of manganese, copper, zinc, iron, and mixtures thereof.

5. The process as recited in claim 4, wherein said cation is manganese.

6. The culture as recited in claim 1, wherein the viability of said transformed culture of cells is at least 12 times greater than the viability of said culture of cells not transformed with said DNA.

7. The transformed culture as recited in claim 1, wherein the viability of said transformed culture of cells is at least 300 times greater than the viability of said culture of cells not transformed with said DNA.

* * * * *

UNITED STATES PATENT AND TRADEMARK OFFICE
CERTIFICATE OF CORRECTION

PATENT NO. : 5,674,721
DATED     : October 7, 1997
INVENTOR(S) : Peter H. Bissinger, Robert H. Schiestl, and John F. Davidson It is certified that error appears in the above-identified patent and that said Letters Patent is hereby corrected as shown below:

Cover page: Replace title, "PROCESS FOR MAKING YEAST CELLS RESISTANT TO EXTREME HIGH PRESSURE," with the following new title:
---PROCESS FOR MAKING YEAST CELLS RESISTANT TO HIGH TEMPERATURE Column 1: Replace title, "PROCESS FOR MAKING YEAST CELLS RESISTANT TO EXTREME HIGH PRESSURE," with the following new title:
---PROCESS FOR MAKING YEAST CELLS RESISTANT TO HIGH TEMPERATURE Signed and Sealed this Twenty-third Day of December, 1997

Attest:

BRUCE LEHMAN

Attesting Officer

Commissioner of Patents and Trademarks